United States Patent [19]

Rachlin et al.

[11] 4,293,549

[45] Oct. 6, 1981

[54] QUINOLINYL GUANIDINES HAVING ANTIINFLAMMATORY, ANALGESIC OR ANTIPYRETIC ACTIVITY

[75] Inventors: Schneur Rachlin, Vaerløse; Edoardo Arrigoni-Martelli, Farum, both of Denmark

[73] Assignee: Leo Pharmaceutical Products Ltd. A/S (Lovens Kemiske Fabrik Produktion-saktieselskab), Ballerup, Denmark

[21] Appl. No.: 955,228

[22] Filed: Oct. 27, 1978

[30] Foreign Application Priority Data

Nov. 7, 1977 [GB] United Kingdom ............ 46166/77

[51] Int. Cl.$^3$ ................. A61K 31/47; A61K 31/555; C07D 215/42
[52] U.S. Cl. ..................... 424/245; 424/248.56; 424/250; 424/251; 424/258; 544/63; 544/64; 544/181; 544/212; 544/225; 544/322; 544/405; 546/9; 546/10; 546/153; 546/157; 546/163
[58] Field of Search ............ 546/163, 156, 157, 159, 546/153, 9, 10; 424/258, 250, 251, 245, 248.56; 544/181, 212, 322, 225, 63, 64, 405

[56] References Cited

U.S. PATENT DOCUMENTS 3,056,789 10/1962 Urech ............................... 546/163
3,159,676 12/1964 Geoffrey et al. ............... 260/564 E
4,000,279 12/1976 Hughes et al. .................. 424/258

FOREIGN PATENT DOCUMENTS 2331246 6/1973 Fed. Rep. of Germany.

OTHER PUBLICATIONS

The Merck Index, 9th ed., Merck & Co., Rahway, N.J. (1976) p. 276.
Durant, et al., J. Med. Chem., vol. 9, pp. 22-27, (1966).
Kishore, et al., Pharmacology, vol. 15, pp. 97-103 (1977).
Raman, et al., Derwent Abstract 35984T (1978).
Lombardino, et al., J. Med. Chem., vol. 16, No. 5, pp. 493-496 (1973).
Wiseman, et al., Biochemical Pharmacology, vol. 21, pp. 2323-2334 (1972).

*Primary Examiner*—Donald G. Daus
*Assistant Examiner*—Diana G. Rivers
*Attorney, Agent, or Firm*—Cushman, Darby & Cushman

[57] ABSTRACT

This invention relates to new compounds, salts, complexes and acylated derivatives thereof, methods of producing said compounds, intermediates used in the method, pharmaceutical compositions containing the present compounds and methods of producing same, and a method of treating patients using the present compounds, having the general formula (I) t,0010 in which $R_1$ represents hydrogen, alkyl, alkoxy, hydroxy, halogen, trifluoromethyl, or phenyl; $R_2$ represents hydrogen, alkyl, alkoxy, halogen, trifluoromethyl, or hydroxy; $R_3$ represents alkyl, cycloalkyl which can be further mono- or disubstituted with methyl or ethyl, phenyl or phenyl-alkyl, optionally being further substituted; and $R_4$ represents a 5- or 6-membered heterocyclic ring system containing at least one nitrogen atom and optionally further nitrogen, oxygen and/or sulphur atoms, said ring system optionally being further substituted; or said ring system optionally forming part of a larger fused ring system; and pharmaceutically acceptable, non-toxic salts, complexes and acylated derivatives thereof.

The present compounds can be used in the therapy of rheumatoid arthritis, osteo-arthritis, and allied conditions in humans and domestic animals by enteral, parenteral or topical administration.

25 Claims, No Drawings

QUINOLINYL GUANIDINES HAVING ANTIINFLAMMATORY, ANALGESIC OR ANTIPYRETIC ACTIVITY

This invention relates to a series of new compounds, to their salts, complexes and acylated derivatives, to methods of producing the said compounds, salts, complexes and acylated derivatives and to intermediates used in the method. Also the invention relates to pharmaceutical compositions containing the compounds and dosage units of the composition, methods of producing such compositions and dosage units, and a method of treating patients using the present compounds.

The new compounds have the general formula (I)

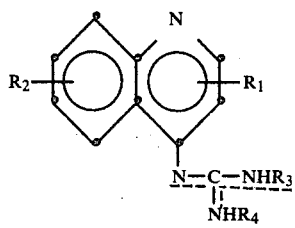

in which $R_1$ represents hydrogen, $C_1$-$C_6$-alkyl, $C_1$-$C_6$-alkoxy, hydroxy, halogen, trifluoromethyl, or phenyl; $R_2$ represents hydrogen, $C_1$-$C_6$-alkyl, $C_1$-$C_6$-alkoxy, halogen, trifluoromethyl, or hydroxy; $R_3$ represents $C_1$-$C_{18}$-alkyl, e.g. methyl, ethyl, propyl, isopropyl, butyl, isobutyl, or tert-butyl radical, or one of the different isomeric pentyl, hexyl, heptyl, octyl, nonyl, decyl, undecyl, dodecyl or octadecyl radicals, or $C_3$-$C_8$-cycloalkyl which can be further mono- or disubstituted with methyl or ethyl, e.g. cyclopropyl, cyclobutyl, cyclopentyl, cyclohexyl or methylcyclohexyl, or phenyl or phenyl-$C_1$-$C_3$-alkyl which can be further substituted with methyl, methoxy, halo, or trifluoromethyl; and $R_4$ represents a 5- or 6-membered heterocyclic ring system containing at least one nitrogen atom and optionally further nitrogen, oxygen and/or sulphur atoms, said ring system optionally being substituted with $C_1$-$C_3$ alkyl, $C_1$-$C_3$-alkoxy, carboxy, carbalkoxy, halogen, trifluoromethyl, hydroxy and/or metcapto; or said ring system optionally forming part of a larger fused ring system.

More particularly, $R_1$ represents hydrogen or $C_1$-$C_4$-alkyl; $R_2$ represents hydrogen or $C_1$-$C_4$-alkyl; $R_3$ represents tertiary $C_4$-$C_{12}$-alkyl, $C_5$-$C_7$-cycloalkyl or phenyl; and $R_4$ represents thienyl, pyrryl, thiazolyl, isothiazolyl, pyrazolyl, imidazolyl, oxazolyl, isoxazolyl, triazolyl, thiadiazolyl, tetrazolyl, pyridyl, pyridazinyl, pyrimidyl, pyrazinyl, triazinyl, oxaxinyl, benzoxazolyl, benzothiazolyl or benzoimidazolyl.

In particular, a preferred group of compounds of formula I comprises those in which $R_1$ represents hydrogen, methyl or ethyl, especially methyl; $R_2$ represents hydrogen; $R_3$ represents tert-butyl, tert-pentyl, cyclohexyl or phenyl; and $R_4$ represents 2-thiazolyl, 2-(4-methylthiazolyl), or 2-(5-methyl-1,3,4-thiadiazolyl).

In formula I above the dotted lines indicate that the compounds may exist in tautomeric forms

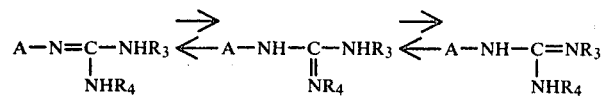

where A indicates the quinolyl moiety.

The present compounds are potent antiinflammatory, analgetic and antipyretic agents, with low acute toxicity and low gastro ulcerogenic activity.

Contrary to almost all of the currently available antiinflammatory drugs the present compounds are basic and form mono- and di-salts with acids among which may be mentioned the non-toxic, pharmaceutically acceptable hydrochloric and hydrobromic acid, phosphoric acid, sulfuric acid, nitric acid, carbonic acid, p-toluenesulfonic acid, methanesulfonic acid, formic acid, acetic acid, propionic acid, citric acid, tartaric acid and maleic acid.

The present compounds and their salts also form complexes with certain metal salts, e.g. Cu-, Zn-, Mn-, Mg-, Fe-, and Au-salts. Both salts and complexes are also therapeutically active and form part of the present invention.

The present compounds can be used in the therapy of rheumatoid arthritis, osteo-arthritis, and allied conditions in humans and domestic animals by enteral, parenteral or topical administration.

In animal experiments, the present compounds have shown interesting superior therapeutical effects. For instance the compound of Example 1 (in the following designated SR 1368) of the present specification has been compared with indomethacin, one of the most widely used and most active antiinflammatory drugs, with the following results:

(1) Acute toxicity

The acute toxicity was determined in mice after oral administration. The mortality was assessed eight days after the administration and the $LD_{50}$ (dose causing the death of 50% of the animals treated) was calculated according to the statistical method of Litchfield and Wilcoxon (J.Pharmacol.Exp.Ther. 96, 99, (1949)). The results are reported in the following table.

|  | $LD_{50}$ mg/kg p.os (with confidence limits) | No. of mice |
|---|---|---|
| SR 1368 | >1000 | 28 |
| Indomethacin | 23 (16-32) | 32 |

(2) Inhibition of carrageenin edema

Inhibitory activity toward carrageenin induced edema was assessed in rats using the technique of Winter C. A., Risley E. A., Nuss C. W. (Proc.Soc.Exp.Biol.Med. 111, 544,(1962)). The compounds were orally administered suspended in 0.5% carboxymethylcellulose to 18 hrs fasting animals, 1 hr before the injection of carrageenin. The results, expressed as percent inhibition of edema development in treated animals as compared to the controls are reported in the following table.

| Compound | Oral dose mg/kg | No. of rats | % Inhibition 3 hrs after carrageenin |
|---|---|---|---|
| SR 1368 | 25 | 8 | 40 |
| SR 1368 | 50 | 8 | 62 |
| SR 1368 | 100 | 8 | 71 |
| Indomethacin | 0.5 | 8 | 34 |
| Indomethacin | 1 | 8 | 42 |
| Indomethacin | 10 | 8 | 65 |

(3) Inhibition of adjuvant induced arthritis

Adjuvant arthritis was produced in rats according to the methods of Walz D. T., Dimartino M. J., Misher A. (Ann.Rheum.Dis. 30, 303,(1971)). The compounds were orally administered suspended in 0.5% carboxymethylcellulose, daily, from the day of adjuvant injection to 28 days later. The results, reported in the following table, indicate the percent inhibition of both primary and secondary swelling as assessed in comparison to controls 18 and 28 days after the adjuvant injection.

| Compound | Daily oral dose mg/kg | No. of rats | % Inhibition of the swelling |||| 
|---|---|---|---|---|---|---|
| | | | 18th day || 28th day ||
| | | | primary | secondary | Primary | secondary |
| SR 1368 | 5 | 8 | 23.5 | 14.9 | 21.4 | 32.1 |
| SR 1368 | 10 | 10 | 29.2 | 54.4 | 42.7 | 68.7 |
| SR 1368 | 30 | 10 | 44.2 | 53.2 | 69.4 | 69.2 |
| SR 1368 | 60 | 10 | 51.6 | 73.4 | 74.2 | 82.6 |
| Indomethacin | 0.3 | 8 | 20.3 | 13.5 | 25.9 | 29.7 |
| Indomethacin | 1 | 8 | 62.4 | 66.2 | 80.5 | 76.8 |

(4) Inhibition of prostaglandin synthetase

Inhibition of prostaglandin synthetase was assessed using lyophilized high speed precipitate of bovine seminal vesicle homogenate as enzyme according to the method of Yanagi Y. and Komatsu T.—Biochem.Pharmacol. 25, 937,(1976). The 50% inhibitory concentrations of SR 1368 and indomethacin are reported in the following table.

| | $IC_{50}$ μM |
|---|---|
| SR 1368 | 2.46 |
| Indomethacin | 1.07 |

(5) Analgetic effect

The analgetic effect was evaluated in rats according to the method of Randall L. and Selitto J. (Arch.Int.Pharmacodyn. 111, 409,(1957)). The results, reported in the following table, indicate the increase of the pain threshold observed 2 hrs after the oral administration of the compounds.

| Compound | Oral dose mg/kg | No. of rats | Increase of pain threshold mmHg |
|---|---|---|---|
| SR 1368 | 10 | 8 | 12 |
| SR 1368 | 30 | 8 | 31 |
| SR 1368 | 90 | 8 | 68 |
| Indomethacin | 1 | 6 | 19 |
| Indomethacin | 3 | 6 | 34 |

(6) Antipyretic effect

The antipyretic activity was determined in rats according to the method of Bianchi C., Lumachi B., Pegrassi L. (Arzn. Forsch. 17, 246,(1967)). The compounds were orally administered and the antipyretic index evaluated over 180 min. of the experiment. The antipyretic indexes are reported in the following table.

| Compound | Oral dose mg/kg | No. of rats | Antipyretic index |
|---|---|---|---|
| SR 1368 | 25 | 8 | 2.2 |
| SR 1368 | 50 | 8 | 5.6 |
| Indomethacin | 3 | 8 | 3.2 |

(7) Gastro ulcerogenic activity

Rats fasted for 9 hrs before treatment were given different doses of the compounds. 24 hrs later the animals were killed, the stomachs were removed, opened along the lesser curvature and gross examined for the presence of lesions and their severity. The severity was assessed according to an arbitrary scale from 0=no lesion to +4=perforation.

| Compounds | Oral dose mg/kg | No. of rats | % with lesions | Mean severity |
|---|---|---|---|---|
| SR 1368 | 25 | 10 | 0 | 0 |
| SR 1368 | 50 | 10 | 20 | 0.9 |
| SR 1368 | 100 | 10 | 40 | 1.7 |
| Indomethacin | 5 | 10 | 20 | 1.3 |
| Indomethacin | 10 | 10 | 70 | 2.8 |

The above data clearly show the outstanding results obtained with the present compounds.

It is another object of the invention to provide a method of producing the compounds of formula I. In one embodiment, a compound of the formula II

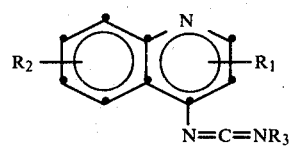

II in which $R_1$, $R_2$ and $R_3$ have the above meanings, is reacted with an amine of the formula III $R_4NH_2$     III in which $R_4$ has the above meanings, or a silylated derivative thereof, capable of reacting with the compound of formula II to form the desired compound of formula I.

In another embodiment, a compound of formula IIa

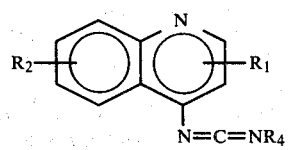

IIa in which $R_1$, $R_2$ and $R_4$ have the above meanings, is reacted with an amine of the formula IIIa $R_3NH_2$    IIIa in which $R_3$ has the above meanings, or a silylated derivative thereof, capable of reacting with the compound of formula IIa to form the desired compound of formula I.

The carbodiimides of formula II and IIa are reactive compounds and therefore preferably reacted with the amines without being purified. They can be obtained as described in Chem. Ber. 104 (1971) p. 1335, from the corresponding thioureas and ureas of the formula IV or IVa,

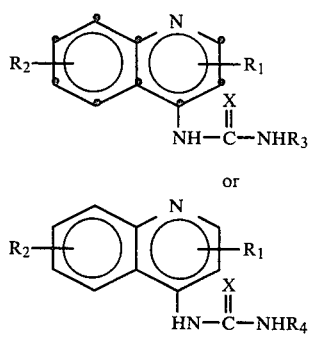

IV or

IVa in which $R_1$, $R_2$, $R_3$, and $R_4$ have the above meanings, and X stands for oxygen or sulphur, by treatment with e.g. triphenylphosphine and carbon tetrachloride in the presence of an acid binding agent such as triethylamine in an inert solvent, e.g. dry methylene chloride, or with phosgene in an inert solvent, e.g. tetrahydrofuran, also in the presence of an acid binding compound, e.g. triethylamine, preferably at low temperatures.

In the method of the invention the reaction between the carbodiimide and the amine is preferably performed in the presence of an inert solvent, e.g. diethyl ether, or another suitable inert solvent. The reaction mixture is left standing for the period of time required to accomplish the reaction. Thus the reaction can take place within 30 minutes to 24 hours, preferably at room temperature, or at higher temperatures, e.g. at the boiling point of a solvent with low boiling point. The compounds of formula I can be isolated by various methods. For instance, in some cases the compounds of formula I may precipitate in crystalline form during the reaction, or they can be recovered by evaporating the reaction mixture, or they can be precipitated by addition of, e.g. petroleum ether, or another similar solvent, to the reaction mixture.

Also the reaction can be performed in the absence of solvent, in which case the compound of formula I formed is recovered by triturating the reaction mixture, e.g. with diethyl ether or petroleum ether.

The compounds of formula I thus obtained are preferably purified by recrystallization from suitable solvents, e.g. cyclohexane, diethyl ether, cyclohexanol, petroleum ether, isopropanol, or mixtures of solvents, e.g. acetone/water, or ethanol/water, but other purification methods can also be used.

Most of the carbodiimides of formula II and IIa used as starting materials in the method of the invention are hitherto unknown compounds and therefore an object of the present invention.

Some of the ureas and thioureas used as starting materials are known from the literature, and the hitherto unknown ones can be prepared by methods analogous to those described. In the following table a number of ureas and thioureas is characterized by their melting points. They are e.g. prepared by reacting the appropriate aminoquinoline or a silylated derivative thereof with a compound $R_3NCX$ in which $R_3$ and X have the above meanings, in an inert solvent, e.g. diethyl ether, dioxane, tetrahydrofuran, benzene, toluene, petroleum ether, dimethylformamide, and at a temperature from about 0° C. to about the boiling point of the solvent used. In some instances, the reaction can advantageously be performed with 1 equivalent of sodium hydride present.

Some thioureas of the formula $$R_4NH-\underset{\underset{S}{\|}}{C}-NHR_3 \qquad V$$

($R_3$ and $R_4$ having the above meanings) are known and the unknown ones can be prepared by reacting 1-1.5 equivalents of an amine $R_3NH_2$ with about 1 equivalent of S-methyl-heterocyclyldithiocarbamate of the formula $R_4NHCSSCH_3$ in a suitable solvent, e.g. diethyl ether, ethanol, chloroform, acetone, pyridine, acetonitrile, and at a temperature from about 0° C. to about the boiling point of the solvent used. For further particulars, see Table A.

TABLE A

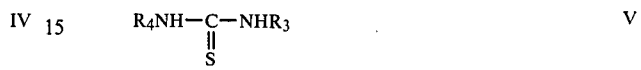

| $R_3$ | $R_1$ | $R_2$ | X | Melting point °C. |
|---|---|---|---|---|
| methyl | 2-$CH_3$— | H | O | 182–184 |
| ethyl | 2-$CH_3$— | H | O | 177–179 |
| ethyl | 2-$CH_3$— | H | S | 192–194 |
| n-propyl | 2-$CH_3$— | H | O | 153–155 |
| isopropyl | 2-$CH_3$— | H | O | 181–183 |
| n-butyl | 2-$CH_3$— | H | O | 168–169 |
| n-butyl | 2-$CH_3$— | 6-$CH_3$— | O | 220–222 (hydrate) |
| sec-butyl | 2-$CH_3$— | H | O | 175–176 |
| isobutyl | 2-$CH_3$— | H | O | 172–174 |
| isobutyl | 2-$CH_3$— | H | S | 215–216(HCl) |
| tert-butyl | 2-$CH_3$— | H | O | 187–189 |
| tert-butyl | 2-$CH_3$— | H | S | 162–164 |
| 2,2-dimethyl-n-propyl | 2-$CH_3$— | H | O | 156–158 |
| isopentyl | 2-$CH_3$— | H | O | 165–167 |
| tert-pentyl | 2-$CH_3$— | H | O | 184–186 |
| tert-pentyl | 2-$CH_3$— | H | S | 140–142 |
| n-hexyl | 2-$CH_3$— | H | S | 152–154 |
| 1,2,2-trimethyl-n-propyl | 2-$CH_3$— | H | O | 206–208 |
| 2-ethyl-n-hexyl | 2-$CH_3$— | H | O | 248–250(HCl) |
| 1,5-dimethyl-n-hexyl | 2-$CH_3$— | H | O | 230–232(HCl) |
| n-decyl | 2-$CH_3$— | H | O | 182–184(HCl) |
| n-decyl | 2-$CH_3$— | H | S | 130–132 |
| octadecyl | 2-$CH_3$— | H | O | 77–79 |
| cyclopropyl | 2-$CH_3$— | H | O | 173–175 |
| cyclopentyl | 2-$CH_3$— | H | O | 167–169 |
| 1-methyl-cyclopentyl | 2-$CH_3$— | H | O | 179–181 |
| cyclohexyl | 2-$CH_3$— | H | O | 124–126 (hydrate) 180–182 (anhydrous) |
| cyclohexyl | 2-$CH_3$— | H | S | 172–174 |
| cyclohexyl | 2-$CH_3$— | 6-$CH_3$— | O | 146–148 |
| 4-methylcyclo- | 2-$CH_3$— | H | O | 205–207 |

TABLE A-continued

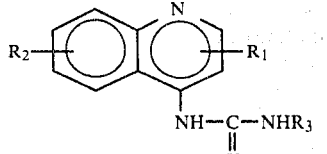

| R₃ | R₁ | R₂ | X | Melting point °C. |
|---|---|---|---|---|
| hexyl | | | | |
| 2,3-dimethyl-cyclohexyl | 2-CH₃— | H | O | 174–176 |
| cyclohexyl-methyl | 2-CH₃— | H | O | 152–154 |
| cycloheptyl | 2-CH₃— | H | O | 185–187 |
| cyclooctyl | 2-CH₃— | H | O | 181–183 |
| phenyl | 2-CH₃— | H | O | 192–194 |
| 2-methylphenyl | 2-CH₃— | H | O | 202–204 |
| 4-methylphenyl | 2-CH₃— | H | O | 185–187 |
| 3,5-dimethyl-phenyl | 2-CH₃— | H | O | 208–210 |
| 2-methoxyphenyl | 2-CH₃— | H | O | 205–207 |
| 4-chlorophenyl | 2-CH₃— | H | O | 199–201 |
| 3-trifluoro-methylphenyl | 2-CH₃— | H | O | 155–157 |
| benzyl | 2-CH₃— | H | O | 188–189 |
| benzyl | 2-CH₃— | H | S | 218–220(HCl) |
| (+)α-phen-ethyl | 2-CH₃— | H | O | 198–200 |
| (−)α-phen-ethyl | 2-CH₃— | H | O | 198–200 |
| furfuryl | 2-CH₃— | H | O | 176–178 |
| tetrahydro-furfuryl | 2-CH₃— | H | O | 136–138 |
| 2-methoxyethyl | 2-CH₃— | H | O | 152–154 |
| 3-dimethylamino-1-n-propyl | 2-CH₃— | H | O | 105–107 |
| isobutyl | H | H | O | 85–87 |
| tert-butyl | H | H | O | 186–188 |
| 1,2,2-trimethyl-n-propyl | H | H | O | >300 |
| n-decyl | H | H | O | 68–70 |
| cyclohexyl | H | H | O | 196–198 |
| cyclohexyl | 2-C₂H₅— | H | O | 189–191 |
| tert-butyl | 2-n-C₃H₇— | H | O | 188–190 |
| cyclohexyl | 2-n-C₃H₇— | H | O | 190–192 |
| tert-butyl | 2-iso-C₃H₇— | H | O | 212–214 |
| cyclohexyl | 2-iso-C₃H₇— | H | O | 217–219 |
| cyclohexyl | 2-iso-C₄H₉— | H | O | 198–200 |
| tert-butyl | 2-iso-C₄H₉— | H | O | 165–167 |
| n-butyl | 2-C₆H₅— | H | O | 206–208 |
| isobutyl | 2-C₆H₅— | H | O | 206–208 |
| sec-butyl | 2-C₆H₅— | H | O | 198–200 |
| tert-butyl | 2-C₆H₅— | H | O | 210–212 |
| cyclohexyl | 2-C₆H₅— | H | O | 231–233 |
| tert-butyl | H | 6-CH₃O— | O | 198–200 |
| cyclohexyl | H | 6-CH₃O— | O | 203–205 |
| tert-butyl | H | 7-Cl— | O | 197–199 |
| cyclohexyl | H | 7-Cl— | O | 228–230 |

| R₄ | R₁ | R₂ | X | Melting point °C. |
|---|---|---|---|---|
| 2-thiazolyl | 2-CH₃— | H | O | 198–200 |
| 2-thiazolyl | H | H | O | 150–152 |
| 2-thiazolyl | 2-C₆H₅— | H | O | 250–252 |

$$R_4HN-\underset{\underset{X}{\|}}{C}-NHR_3$$

| R₄ | R₃ | X | Melting point °C. |
|---|---|---|---|
| 2-thiazolyl | tert-butyl | O | 144–146 |
| 2-thiazolyl | sec-butyl | S | 75–77 |
| 2-thiazolyl | isobutyl | S | 132–134 |
| 2-thiazolyl | 1-ethylpropyl | S | 108–110 |
| 2-thiazolyl | neopentyl | S | 190–191 |
| 2-thiazolyl | 1,1,3,3-tetra-methyl-n-butyl | S | 111–113 |
| 2-thiazolyl | cyclohexyl | S | 159–161 |
| 2-thiazolyl | cyclooctyl | S | 111–113 |
| 2-benzothiazolyl | tert-butyl | O | 301–303 |
| 2-(5-methyl-1,3,4-thiadiazolyl) | tert-butyl | O | more than 300 |
| 2-thiazolyl | 4-methylcyclo-hexyl | S | 194–196 |
| 2-thiazolyl | 4-methylphenyl | S | 192–194 |
| 2-thienyl | tert-butyl | O | 192–194 |
| 2-thienyl | cyclohexyl | O | 217–219 |

The hitherto unknown ureas and thioureas of formula IV used as intermediates are also within the scope of the present invention.

In still another embodiment of the method of the invention, a compound of the formula VI $$R_4N=C=NR_3 \qquad\qquad VI$$

in which R₃ and R₄ have the above meanings, is reacted with a 4-aminoquinoline derivative of the formula VII

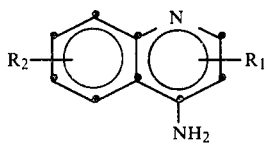
VII or a silylated derivative thereof, in which R₁ and R₂ have the above meanings to form the desired compound of formula I. The reaction conditions are similar to those described in connection with the previous embodiments.

The carbodiimides of formula VI are prepared analogously with the carbodiimides of formula II.

The compounds of formula I can according to the invention also be prepared from a reactive derivative of the starting substance of formula IV, e.g. by reacting a compound of formula VIII or a salt thereof

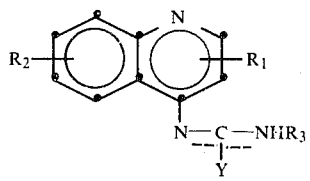
VIII or

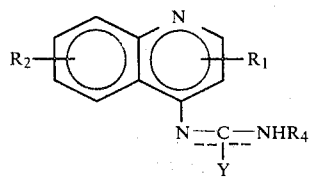
VIIIa in which $R_1$, $R_2$, $R_3$ and $R_4$ have the meaning hereinbefore defined and Y stands for halogen, S-lower alkyl or O-lower alkyl, with an amine of formula III or IIIa, respectively, or a silylated derivative thereof. The reaction is appropriately carried out in the presence of an inert solvent, and when Y stands for halogen, an acid binding agent, such as a tertiary amine, is preferably added and can act as a solvent, when used in excess.

The substances of formula VIII or VIIIa are either known compounds or can be produced analogous to known compounds by methods known from the literature. For further particulars, see table B.

TABLE B

| Y | $R_3$ | Melting point °C. |
|---|---|---|
| $CH_3O-$ | $t$-$C_4H_9$ | 151–153 |
| $C_2H_5O-$ | $t$-$C_4H_9$ | 161–163 |
| $n$-$C_3H_7O-$ | $t$-$C_4H_9$ | 110–112 |
| $C_2H_5S-$ | $t$-$C_4H_9$ | 146–148 |
| $n$-$C_3H_7S-$ | $t$-$C_4H_9-$ | 158–160 |
| $i$-$C_4H_9S-$ | $t$-$C_4H_9-$ | 141–142 |
| $CH_3O-$ | 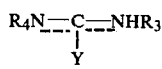 | 190–192 |
| $C_2H_5O-$ | 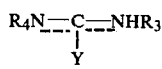 | 148–150 |
| $n$-$C_3H_7O-$ | 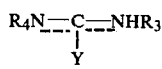 | 134–136 |
| $n$-$C_4H_9O-$ | 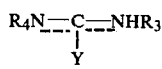 | 128–130 |
| $i$-$C_4H_9O-$ | 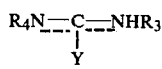 | 146–148 |
| $C_2H_5S-$ | 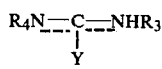 | 134–136 |
| $n$-$C_3H_7S-$ | 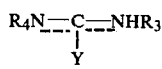 | 114–116 |
| $i$-$C_4H_9S-$ | 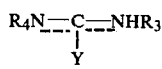 | 144–146 |

In still another embodiment of the invention the compounds of formula I can be produced by reacting an aminoquinoline of formula VII in which $R_1$ and $R_2$ have the meaning hereinbefore defined, or a silylated derivative thereof, with a compound of formula IX $$R_4N=C-NHR_3 \quad\quad IX$$
$$|$$
$$Y$$

in which $R_3$, $R_4$, and Y have the above meanings, to form the desired compound of formula I.

The reaction is carried out in a manner known per se and preferably in an inert solvent in the presence of an acid binding substance in case Y stands for halogen. The substances of formula VII are known compounds. Some of the compounds of formula IX are known from the literature, and hitherto unknown compounds of formula IX can be prepared by methods analogous to those described for preparing the known compounds. The starting substances of formula IX which are new compounds form part of the present invention as intermediates.

In the event the intermediates used in the methods contain reactive radicals as substituents, which may interfere with the reaction of the methods disclosed hereinbefore the radicals, e.g. amino groups or hydroxy groups, can be temporarily protected during the reaction in a manner known per se.

The present compounds can further be directly acylated to form acylated guanidines, which also can be prepared by using, in the above methods, acylated intermediates prepared from compounds of formulae III, IIIa and VII.

These compounds are also therapeutically active and form part of the present invention.

In general, if one of the substituents $R_2$ or $R_4$ of the final compound of formula I is or contains a reactive radical as substituent, it is preferred to use one of the above methods in which the $R_2$ or $R_4$ containing substituent is introduced in the last step.

If salts of the compounds of formula I are desired, they can be produced by simple neutralization of the compound with the acid in question in the presence of a suitable reaction medium facilitating the reaction, and from which the salt may precipitate or, if necessary, can be precipitated by adding a suitable component to depress the solubility of the desired salt, or the salt can be isolated by evaporation of the reaction mixture.

The salts can in some cases also be obtained directly by reacting the corresponding amine salt with the carbodiimide.

Alternatively a salt of a compound of formula I prepared in advance can be reacted with the acid in question, or the desired salt of a compound of formula I can be prepared by a double decomposition of a previously prepared salt of the compound of formula I and another salt containing the desired anion, or acid.

Mono- or di-salts are obtained depending on the ratio between the reactants of the salt formation.

The water-soluble salts of the compounds of formula I may be preferred as active substances in the composition of the invention. On the other hand, for therapeutic purposes requiring a special resorption rate of the drug it may be advantageous to use sparingly water-soluble salts with suitable non-toxic acids or the free base of compounds of formula I which normally are sparingly soluble in water.

It is a further object of the present invention to provide pharmaceutical compositions which are useful, e.g. in the treatment of patients.

With this object in view, the compositions of the invention contain as an active component at least one member selected from the group consisting of compounds of the formula I and salts thereof with non-toxic, pharmaceutically acceptable acids, together with solid or liquid pharmaceutical carriers and/or auxiliary agents.

Said composition should contain at least one 0.1% of the therapeutically active compound and can be worked up to various pharmaceutical forms of presentation, such as tablets, pills, dragees, capsules, sustained release tablets, suspensions, ointments, creams, lotions, suppositories, injection medicine, containing the compounds of formula I or their atoxic salts, complexes or acylated derivatives, mixed with carriers and/or auxiliary agents.

Pharmaceutical organic or inorganic, solid or liquid carriers and/or auxiliary agents suitable for enteral, parenteral or topical administration can be used to make up compositions containing the present compounds. Gelatine, lactose, starch, magnesium stearate, talc, vegetable and animal fats and oils, gum, polyalkylene glycol, buffers or other known carriers and/or auxiliary agents for medicaments are all suitable.

In addition the compositions may contain other therapeutic compounds, e.g. other antiinflammatory agents, analgetics and antipyretics, which might give rise to a synergistic effect.

Another object of the invention resides in the selection of a dose of the compounds of the invention which dose can be administered so that the desired activity is achieved without simultaneous secondary effects.

In the human therapy, the compounds and their salts can conveniently be administered (to adults) in dosage units containing not less than 10 mg and up to 1000 mg, preferably from 25 mg to 500 mg, calculated as the free bases of formula I, together with a pharmceutically acceptable, non-toxic carrier.

By the term "dosage unit" is meant a unitary, i.e. a single dose which is capable of being administered to a patient, and which may be readily handled and packed, remaining as a physically stable unit dose comprising either the active material as such, or a mixture of it with solid or liquid pharmaceutical diluents or carriers.

In the form of dosage units, the compounds may be administered once or more times a day at appropriate intervals, always depending, however, on the condition of the patient, and in accordance with the prescription made by the medical practitioner.

The adequate daily dose of the compounds of formula I, or their salts, is within the range from 1 mg/kg body weight/day to 30 mg/kg body weight/day.

For parenteral use, e.g. injections, the compounds of the invention are given e.g. in an aqueous solution or suspension as a dosage unit containing from 0.1 g to 1 g of the compound, calculated as the free base to be dissolved or suspended immediately before use, or ready for use together with a pharmaceutically acceptable vehicle.

In the continuous therapy tablets or capsules may be the appropriate form of pharmaceutical preparation owing to the long-lasting effects obtained when the drug is given orally, or sustained release formulations can also support the long-lasting effect of the compounds of formula I.

The invention will be further described in the following Examples which are not construed as limiting the invention.

EXAMPLE 1

N-Cyclohexyl-N''-4-(2-methylquinolyl)-N'-2-thiazolyl-guanidine. (SR 1368)

A. N-Cyclohexyl-N'-4-(2-methylquinolyl)carbodiimide

A stirred mixture consisting of N-cyclohexyl-N'-4-(2-methylquinolyl)urea (283.0 g), triethylamine (75.0 ml), carbon tetrachloride (50 ml), triphenylphosphine (150 g) and dry methylene chloride (1.0 l) is refluxed for 2 hours. The mixture is concentrated under reduced pressure, and the residue is extracted with 4 portions of boiling petroleum ether (b.p. <50° C.) (2.0 l).

The combined extracts are evaporated in vacuo to yield the crude carbodiimide in high yield.

IR (CHCl$_3$): strong absorption band at 2140 cm$^{-1}$ (N=C=N).

B.

N-Cyclohexyl-N''-4-(2-methylquinolyl)-N'-2-thiazolyl-guanidine

2-Aminothiazole (73.0 g) was added to crude N-cyclohexyl-N'-4-(2-methylquinolyl)carbodiimide (209.0 g), and the mixture was heated on a steam bath for 1 hour and allowed to cool to room temperature.

The mixture was triturated with 400 ml of ethyl acetate. The crystalline precipitate was collected and had a m.p. of 194°–195° C. after recrystallization from 1-propanol.

A solution of the free base in ethanol was converted to the hydrochloride by treatment with an equivalent amount of a solution of 1 mole of hydrogen chloride in ethanol, the monohydrochloride having a m.p. of 236°–237° C.

The dihydrochloride was prepared by using an excess of hydrogen chloride in ethanol and had a m.p. of 234°–235° C.

The Zn-complex was prepared by adding anhydrous ZnCl$_2$ (0.75 g) in 10.0 ml of absolute ethanol to a solution of SR 1368 HCl (2.0 g) in 20.0 ml of absolute ethanol. The precipitated complex was filtered off giving the analytically pure compound with a m.p. of 247°–249° C. C$_{20}$H$_{23}$N$_5$S.HCl.ZnCl$_2$ (white crystals).

Analogously, the following complexes were prepared:

CoCl$_2$.C$_{20}$H$_{23}$N$_5$S.HCl m.p. 152°–154° C. (blue crystals)

CuCl$_2$.C$_{20}$H$_{23}$N$_5$S.HCl m.p. 174°–176° C. (brown crystals)

½ MnCl$_2$.H$_2$O C$_{20}$H$_{23}$N$_5$S m.p. 215°–217° C. (white crystals)

NMR spectrum for the title compound (10% w/v CDCl$_3$):

| Group | H count | Multiplicity | δ (ppm) |
|---|---|---|---|
| —CH$_2$—CH$_2$\\ <br> $\quad\quad\quad$ CH$_2$ <br> —CH$_2$—CH$_2$/ | 10 H | m | 0.9–2.3 |
| N—C(CH$_3$) (ring) | 3 H | s | 2.60 |
| —HN—CH | 1 H | m | 4.00 |
| thiazole S—CH=CH—N | 1 H <br> 1 H | d, J = 4 <br> d, J = 4 | 6.72 <br> 7.33 |
| quinoline H | 1 H | s | 7.18 |
| quinoline H | 4 H | m | 7.2–8.2 |

In this and the following examples, the chemical shifts are given as ppm δ values with TMS (0 ppm) as internal standard.

Coupling constants (J) are in cps.

EXAMPLES 2-16

By following the procedure described in Example 1, but replacing 2-aminothiazole with other amines of the formula $R_4NH_2$, $R_4$ having the meanings given in Table B′, the corresponding guanidine derivatives were obtained, as indicated in Table B′:

TABLE B1

| Ex. No. | $R_4$ | Melting point °C. |
|---|---|---|
| 2 | 4-methyl-2-thiazolyl | 180–182 |
| 3 | 4,5-dimethyl-2-thiazolyl | 180–182 |
| 4 | 5-ethoxycarbonyl-2-thiazolyl | 170–172 |
| 5 | 4-ethoxycarbonyl-2-thiazolyl | 228–230 |
| 6 | 5-carboxy-2-thiazolyl | 238–240 |
| 7 | 4-carboxy-2-thiazolyl | 198–200 |
| 8 | 4,5,6,7-tetrahydrobenzothiazol-2-yl | 184–186 |
| 9 | 3-methyl-5-isothiazolyl | 226–228 |
| 10 | 1,3,4-thiadiazol-2-yl | 217–219 |
| 11 | 5-methyl-1,3,4-thiadiazol-2-yl | 246–248 |
| 12 | 5-mercapto-1,3,4-thiadiazol-2-yl | 172–174 |
| 13 | 3,5-dimethylisoxazol-4-yl | 218–220 |
| 14 | imidazol-2-yl | 102–104 |
| 15 | benzothiazol-2-yl | 199–201 |
| 16 | 2-pyridyl | 206–208 |

EXAMPLE 17

N-tert-Butyl-N″-4-(2-methylquinolyl)-N′-2-thiazolylguanidine

2-Aminothiazole (1.0 g) was added to crude N-tert-butyl-N′-4-(2-methylquinolyl)carbodiimide (2.8 g). The mixture was heated on a steam bath for 15 minutes and allowed to cool to room temperature. After 12 hours the mixture was triturated with 25 ml of diethyl ether. The crystalline precipitate formed was collected. It was analytically pure and had m.p. 194°–196° C.

NMR spectrum (10% w/v $(CD_3)_2SO$):

| | | | |
|---|---|---|---|
| $C(CH_3)_3$ | 9 H | s | 1.47 |
| —$CH_3$ | 3 H | s | 2.41 |
| thiazole | { 1 H<br> 1 H | d, J = 4<br>d, J = 4 | 6.83 }<br>7.27 |
| benzene ring | 4 H | m | 7.2–8.3 |
| quinoline H | 1 H | bs | 7.63 |

EXAMPLES 18-28

By following the procedure described in Example 17, but replacing 2-aminothiazole with other amines of the formula $R_4NH_2$, $R_4$ having the meanings given in Table C, the corresponding guanidine derivatives were obtained, as indicated in Table C:

TABLE C

| Ex. No. | $R_4$ | Melting point °C. |
|---|---|---|
| 18 | 4-methyl-2-thiazolyl | 205–207 |
| 19 | 4,5-dimethyl-2-thiazolyl | 190–192 |
| 20 | 5-ethoxycarbonyl-2-thiazolyl | 174–176 |
| 21 | 4-ethoxycarbonyl-2-thiazolyl | 188–190 |
| 22 | benzothiazol-2-yl | 200–202 |

TABLE C-continued

Structure:
quinoline (2-CH3) with 4-position: N=C(-NHC(CH3)2CH3)-NHR4

| Ex. No. | R4 | Melting point °C. |
|---------|-----|-------------------|
| 23 | CH3-thiadiazolyl (S, N—N) | 214–216 |
| 24 | HS-thiadiazolyl (S, N—N) | 150–152 |
| 25 | N-methyl-tetrazolyl | 264–265 |
| 26 | methylthienyl | 193–195 |
| 27 | pyridyl | 224–226 |
| 28 | pyrimidinyl | 201–203 |

EXAMPLE 29

N-Ethyl-N''-4-(2-methylquinolyl)-N'-2-thiazolylguanidine

By following the procedure of Example 1 but replacing N-cyclohexyl-N'-4-(2-methylquinolyl)carbodiimide with N-ethyl-N'-4-(2-methylquinolyl)carbodiimide, the title compound was prepared, having a m.p. of 183°–185° C. (after recrystallization from ethyl acetate).

NMR spectrum (10% w/v CDCl$_3$).

| | | | |
|---|---|---|---|
| CH$_3$—CH$_2$— | 3 H | t, J = 7 | 1.25 |
| CH$_3$—CH$_2$— | 2 H | m | 3.50 |
| quinoline-CH$_3$ | 3 H | s | 2.51 |
| quinoline-H | 1 H | bs | 7.08 |
| thiazole-H (S,N) | 1 H | d, J = 4 | 6.66 |
| thiazole-H | 1 H | d, J = 4 | 7.27 |
| aromatic (benzo) | 4 H | m | 7.2–8.2 |

EXAMPLE 30

N''-4-(2-Methylquinolyl)-N-tert-pentyl-N'-2-thiazolylguanidine

By following the procedure of Example 1 but replacing N-cyclohexyl-N'-4-(2-methylquinolyl)carbodiimide with N-4-(2-methylquinolyl)-N'-tert-pentylcarbodiimide, the title compound was prepared, having a m.p. of 164°–165° C. (after recrystallization from ethyl acetate).

NMR spectrum (10% w/v in 1:7-DCl:D$_2$O).

| | | | |
|---|---|---|---|
| —CH$_2$—CH$_3$ | 3 H | t, J = 7 | 1.28 |
| —CH$_2$—CH$_3$ | 2 H | q, J = 7 | 1.92 |
| —C(CH$_3$)$_2$— | 6 H | s | 1.50 |
| quinoline-CH$_3$ | 3 H | s | 2.75 |
| quinoline-H | 1 H | s | 6.90 |
| thiazole-H | 1 H | d, J = 4 | 7.00 |
| thiazole-H | 1 H | d, J = 4 | 7.37 |
| aromatic (benzo) | 4 H | m | 7.4–8.4 |

EXAMPLE 31

N-tert-Butyl-N''-4-(2-methylquinolyl)-N'-2-thiazolylguanidine

By following the procedure of Example 17, but replacing N-tert-butyl-N'-4-(2-methylquinolyl)carbodiimide with N-tert-butyl-N'-2-thiazolylcarbodiimide and 2-aminothiazole with 4-amino-2-methylquinoline, the title compound was produced and was identical with the compound produced according to Example 17.

EXAMPLE 32

N''-4-(2-Methylquinolyl)-N-2-thiazolyl-N'-(1,1,3,3-tetramethyl-n-butyl)guanidine By following the procedure of Example 31 but replacing N-tert-butyl-N'-2-thiazolylcarbodiimide with N-2-thiazolyl-N'-(1,1,3,3-tetramethyl-n-butyl)carbodiimide the title compound was produced having a m.p. of 173°–175° C. (after recrystallization from diethyl ether).

NMR spectrum (10% w/v CDCl$_3$).

| | | | |
|---|---|---|---|
| C(CH$_3$)$_3$ | 9 H | s | 1.00 |
| —C(CH$_3$)$_2$— | 6 H | s | 1.57 |
| —CH$_2$— | 2 H | s | 1.92 |
| quinoline-CH$_3$ | 3 H | bs | 4.38 |

TABLE F-continued

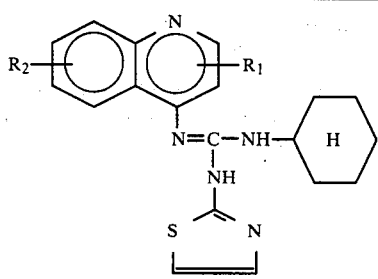

| Ex. No. | R₁ | R₂ | Melting point °C. |
|---|---|---|---|
| 73 | 2-CH₃— | 3-Cl— | 244–245 |

EXAMPLES 74-77

By following the procedure of Example 31, but replacing 4-amino-2-methylquinoline with amines of formula VII having $R_1$ and $R_2$ as indicated in the below table the corresponding guanidine derivatives are obtained as indicated in the below table G:

TABLE G

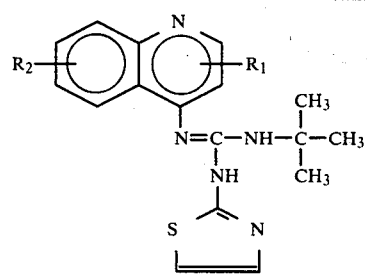

| Ex. No. | R₁ | R₂ | Melting point °C. |
|---|---|---|---|
| 74 | 2-C₂H₅O— | H | 122–124 (base) |
|  |  |  | 145–147 (dinitrate) |
| 75 | 2-Cl— | H | 164–166 |
| 76 | H | 7-CF₃— | 200–202 |
| 77 | 2-CF₃— | H | 185–187 |

EXAMPLES 78-87

By following the procedure of Example 17, but replacing N-tert-butyl-N'-4-(2-methylquinolyl)carbodiimide with carbodiimides of formula II ($R_1$, $R_2$ and $R_3$ having the meanings as indicated in the below table H), the corresponding guanidine derivatives are obtained, as indicated in the below table H:

TABLE H

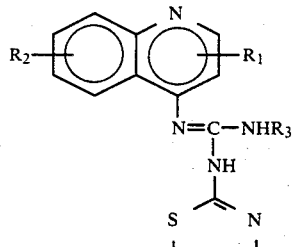

| Ex. No. | R₁ | R₂ | R₃ | Melting point °C. |
|---|---|---|---|---|
| 78 | H | H | tert-C₄H₉— | 172–174 |

TABLE H-continued

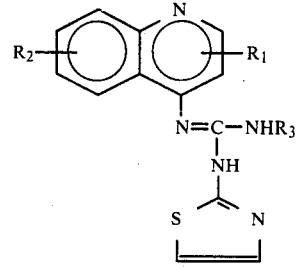

| Ex. No. | R₁ | R₂ | R₃ | Melting point °C. |
|---|---|---|---|---|
| 79 | H | H | CH₃—C(CH₃)(CH₃)—CH(CH₃)— | 108–110 |
| 80 | 2-CH₃— | 6-CH₃— | tert-C₄H₉— | 180–182 |
| 81 | 2-n-C₃H₇— | H | tert-C₄H₉— | 175–176 |
| 82 | 2-iso-C₃H₇— | H | tert-C₄H₉— | 162–164 |
| 83 | 2-iso-C₄H₉— | H | tert-C₄H₉— | 159–160 |
| 84 | 2-C₆H₅— | H | tert-C₄H₉— | 181–183 |
| 85 | 2-C₆H₅— | H | iso-C₄H₉— | 150–151 |
| 86 | H | 6-CH₃O— | tert-C₄H₉— | 162–164 |
| 87 | H | 7-Cl— | tert-C₄H₉— | 180–182 |

EXAMPLE 88

N-Cyclohexyl-N''-4-(2-methylquinolyl)-N'-3-(1,2,4-triazinyl)guanidine

By following the procedure described in Example 1, but replacing 2-aminothiazole with 3-amino-1,2,4-triazine, the title compound was obtained.

EXAMPLE 89

N-Cyclohexyl-N''-4-(2-methylquinolyl)-N'-2-(1,3,5-triazinyl)guanidine

By following the procedure described in Example 1, but replacing 2-aminothiazole with 2-amino-1,3,5-triazine, the title compound was obtained.

EXAMPLE 90

N-Cyclohexyl-N''-4-(2-methylquinolyl)-N'-2-thiazolylguanidine

A.

N-Cyclohexyl-N'-4-(2-methylquinolyl)-S-ethylisothiourea

A solution of N-cyclohexyl-N'-4-(2-methylquinolyl)-carbodiimide (5.4. g) in 10 ml of toluene and ethanethiol (2.5 ml) was heated on a steam bath for 16 hours, and allowed to cool to room temperature.

The mixture was triturated with diethyl ether, and the crystalline precipitate was collected and had a m.p. of 134°–136° C.

B.

N-Cyclohexyl-N''-4-(2-methylquinolyl)-N'-2-thiazolylguanidine

N-Cyclohexyl-N'-4-(2-methylquinolyl)-S-ethylisothiourea (330 mg) was refluxed with 2-aminothiazole (100 mg) in 2.0 ml of toluene.

After refluxing for 150 hours, the solution was evaporated to dryness under reduced pressure, and the residue was triturated with diethyl ether, the title compound was obtained with a m.p. of 190°–191° C.

-continued

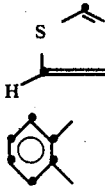

| | 1 H | d, J = 4 | 6.72 |
| | 1 H | d, J = 4 | 7.33 |
| | 4 H | m | 7.0–8.2 |

EXAMPLES 33–56

By following the procedure of Example 1, but replacing N-cyclohexyl-N'-4-(2-methylquinolyl)carbodiimide with the corresponding carbodiimide of formula II ($R_1$=2-$CH_3$, $R_2$=H, and $R_3$ having the meanings as indicated in the below Table D), the corresponding guanidine derivatives were obtained, as indicated in the below Table D:

TABLE D

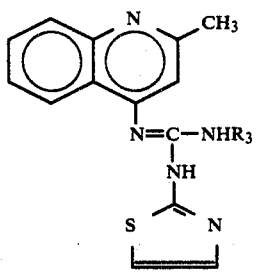

| Ex. No. | $R_3$ | Melting point °C. |
|---|---|---|
| 33 | n-$C_4H_9$— | 156–158 |
| 34 | iso-$C_4H_9$— | 146–147 |
| 35 | sec-$C_4H_9$— | 152–154 |
| 36 | $CH_3$—$\overset{\overset{CH_3}{\mid}}{\underset{\underset{CH_3}{\mid}}{C}}$—$CH_2$— | 176–178 |
| 37 | $CH_3$—$\overset{\overset{CH_3}{\mid}}{\underset{\underset{CH_3}{\mid}}{C}}$——$\overset{\overset{CH_3}{\mid}}{CH}$— | 184–185 |
| 38 | 2-ethyl-n-hexyl- | 127–129 (dinitrate) |
| 39 | 1,5-dimethyl-n-hexyl- | 130–131 (dinitrate) |
| 40 | n-decyl- | 130-decomp. (dinitrate) |
| 41 | octadecyl- | 146–148 (dihydrochloride) |
| 42 | cyclopropyl- | 143-decomp. (dinitrate) |
| 43 | cyclopentyl- | 196–198 |
| 44 | 1-methylcyclopentyl- | 183–185 |
| 45 | cyclohexylmethyl- | 131–132 (dinitrate) |
| 46 | 4-methylcyclohexyl- | 170–171 |
| 47 | 2,3-dimethylcyclohexyl- | 166–167 (hydrochloride) |
| 48 | cycloheptyl- | 167–169 |
| 49 | cyclooctyl- | 145–147 |
| 50 | (−)-α-phenethyl- | 176–178 (dihydrochloride, dihydrate) |
| 51 | (+)-α-phenethyl- | 176–180 (dihydrochloride, dihydrate) |
| 52 | phenyl- | 208–210 |
| 53 | 2-methylphenyl- | 177–179 |
| 54 | 4-methylphenyl- | 192–194 |
| 55 | 2-methoxyphenyl- | 200–202 |
| 56 | 4-chlorophenyl- | 194–196 |

EXAMPLE 57

N-Cyclohexyl-N''-4-(2-methylquinolyl)-N'-2-($\Delta^2$-thiazolinyl)guanidine

By following the procedure of Example 1, but replacing 2-aminothiazole with 2-amino-$\Delta^2$-thiazoline, the title compound was obtained having a m.p. 129°–131° C. (after recrystallization from diethyl ether).

EXAMPLES 58–63

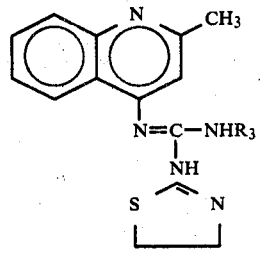

By following the procedure of Example 57, but replacing N-cyclohexyl-N'-4-(2-methylquinolyl)carbodiimide with the corresponding carbodiimides of formula II ($R_1$=2-methyl, $R_2$=H and $R_3$ having the below values), the corresponding guanidine derivatives were obtained, as indicated in the below table E:

TABLE E

| Ex. No. | $R_3$ | Melting point °C. |
|---|---|---|
| 58 | $CH_3$— | 129–131 |
| 59 | $C_2H_5$— | 124–126 |
| 60 | n-$C_3H_7$— | 118–120 |
| 61 | n-$C_4H_9$— | 116–118 |
| 62 | t-$C_4H_9$— | 195–197 |
| 63 | t-$C_5H_{11}$— | 165–167 |

EXAMPLES 64–73

By following the procedure of Example 1, but replacing N-cyclohexyl-N'-4-(2-methylquinolyl)-carbodiimide with the corresponding carbodiimides of formula II ($R_1$ and $R_2$ having the meanings as indicated in the below Table F), the corresponding guanidine derivatives were obtained, as indicated in the below Table F:

TABLE F

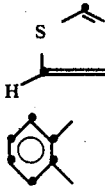

| Ex. No. | $R_1$ | $R_2$ | Melting point °C. |
|---|---|---|---|
| 64 | H | H | 195–197 |
| 65 | 2-$C_2H_5$— | H | 185–187 |
| 66 | 2-n-$C_3H_7$— | H | 174–176 |
| 67 | 2-iso-$C_3H_7$— | H | 168–170 |
| 68 | 2-iso-$C_4H_9$— | H | 169–171 |
| 69 | 2-$C_6H_5$— | H | 149–151 |
| 70 | 2-$CH_3$— | 6-$CH_3$— | 195–197 |
| 71 | H | 6-$CH_3O$— | 168–170 |
| 72 | H | 7-Cl— | 195–197 |

EXAMPLE 91

N-tert-Butyl-N″-4-(2-methylquinolyl)-N′-2-thiazolyl-guanidine

A. N-tert-Butyl-N′-2-thiazolyl-S-methylisothiourea, iodide

Methyl iodide (0.76 ml) was added dropwise over a period of 5 minutes to a refluxing solution of N-tert-butyl-N′-thiazolylthiourea (2.2 g) in 10 ml of methanol. After refluxing for 1 hour the solution was evaporated to dryness under reduced pressure. The crude solid was triturated with diethylether and gave the analytically pure compound with a m.p. of 167°–169° C.

B. N-tert-Butyl-N″-4-(2-methylquinolyl)-N′-2-thiazolyl-guanidine

The compound obtained in step A of this Example was reacted with 4-amino-2-methylquinoline and gave the desired compound with a m.p. of 192°–194° C.

EXAMPLE 92

N-Acetyl-N′-cyclohexyl-N″-4-(2-methylquinolyl)-N-2-thiazolylguanidine

A. 2-Acetamidothiazole (1.4 g) was stirred in dry dimethylformamide (10.0 ml), and NaH (0.5 g; 50% mineral oil dispersion) was added, followed by N-cyclohexyl-N′-4-(2-methylquinolyl)carbodiimide (2.7 g). The mixture was stirred for 4 hours at room temperature, and thereafter evaporated in vacuo. After trituration with petroleum ether, H$_2$O (15.0 ml) was added, and pH was adjusted to 7 by addition of KH$_2$PO$_4$ (1.5 g) in H$_2$O (10 ml) and dilute 2 N ammonium hydroxide. The precipitate was filtered off, dried and had a m.p. of 151°–153° C.

B. The title compound could also be prepared by stirring N-cyclohexyl-N″-4-(2-methylquinolyl)-N′-2-thiazolylguanidine (32.0 g) with acetic anhydride (220 ml). After 10 min. of stirring, a clear solution was obtained which after stirring at room temperature for 20 hours, successively solidified. The crude product was collected, washed with ethylacetate, water, acetone, and ether and has a m.p. of 158°–160° C.

EXAMPLE 93

N-Cyclohexyl-N″-4-(2-methylquinolyl)-N′-propionyl-N′-2-thiazolylguanidine, dihydrate By following the procedure of Example 92A, but replacing 2-acetamidothiazole with 2-propionamido-thiazole, the title compound was obtained having a m.p. of 140°–142° C.

EXAMPLE 94

N-Acetyl-N′-tert-butyl-N″-4-(2-methylquinolyl)-N-2-thiazolylguanidine

By following the procedure of Example 92B, but replacing N-cyclohexyl-N″-4-(2-methylquinolyl)-N′-2-thiazolylguanidine with N-tert-butyl-N″-4-(2-methyl-quinolyl)-N′-2-thiazolylguanidine, the title compound was obtained having a m.p. of 150°–152° C.

EXAMPLE 95

1000 Tablets, each containing 250 mg of SR-1368, HCl

| Ingredients: | | |
|---|---|---|
| SR-1368, HCl | I | 250 g |
| Corn starch | | 42 g |
| Lactose | | 20 g |
| Methylcellulose | | 5 g |
| Magnesium stearate | | 3 g |
| Silicium dioxide | | 2 g |

I is granulated, the granules are broken and mixed with magnesium stearate and silicium dioxide. The granulate is compressed into tablets, yielding 1000 tablets each containing 250 mg of SR-1368, HCl.

EXAMPLE 96

1000 Capsules, each containing 250 mg of SR-1368, HCl

| Ingredients: | | |
|---|---|---|
| SR-1368, HCl | I | 250 g |
| Corn starch | | 150 g |
| Lactose | | 50 g |
| Methylcellulose | | 5 g |
| Magnesium stearate | | 6 g |

I is granulated, the granules are broken and mixed with magnesium stearate. The granulate is filled into gelatine capsules, using a semi-automatic capsule-filling machine shaken by vibrator. Each capsule contains 250 mg of SR-1368, HCl.

EXAMPLE 97

Ointment containing 5% SR-1368, HCl

| Ingredients: | | |
|---|---|---|
| SR-1368, HCl | | 50 g |
| Tween 60 | I | 60 g |
| Glycerine | | 105 g |
| Water | | 420 g |
| Cetyl alcohol | | 105 g |
| White petrolatum | II | 60 g |
| Liquid paraffin | | 105 g |
| Butylhydroxyanisole | | 0.038 g |
| Tween 80 | | 0.285 g |
| Silicone antifoam | III | 0.075 g |
| Potassium sorbate | | 2 g |
| Water | | 93 g |

A solution of I is produced by heating the components.

The components of II are melted together on a steam-bath at 70°–80° C.

I and II are mixed together at 65° C. and the mixture is allowed to cool until room temperature with stirring. Thereafter, a solution of III is added. The SR-1368, HCl is sieved through a 0.3 mm sieve and triturated gradually with the ointment base.

What we claim is:

1. A compound of the formula I having anti-inflammatory, analgesic or antipyretic activity and characterized by its low acute toxicity and low gastro ulcerogenic activity

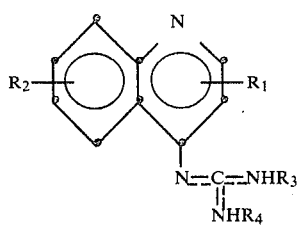

in which $R_1$ represents hydrogen, $C_1$-$C_6$-alkyl, $C_1$-$C_6$-alkoxy, hydroxy, halogen, trifluoromethyl, or phenyl; $R_2$ represents hydrogen, $C_1$-$C_6$-alkyl, $C_1$-$C_6$-alkoxy, halogen, trifluoromethyl, or hydroxy; $R_3$ represents $C_1$-$C_{18}$-alkyl, $C_3$-$C_8$-cycloalkyl which is unsubstituted or mono- or di-substituted with methyl or ethyl, or phenyl or phenyl-$C_1$-$C_3$-alkyl in which the phenyl is unsubstituted or substituted with a methyl, methoxy, halo or trifluoromethyl group; and $R_4$ represents a heterocyclic ring system selected from thiazolinyl, thienyl, pyrryl, thiazolyl, isothiazolyl, pyrazolyl, imidazolyl, oxaxolyl, isoxazolyl, triazolyl, thiadiazolyl, tetrazolyl, pyridyl, pyridazinyl, pyrimidyl, pyrazinyl, triazinyl, oxazinyl, benzoxazolyl, benzothiazolyl and benzoimidazolyl, said ring system being unsubstituted or substituted with from 1 to 2 members of the group consisting of $C_1$-$C_3$-alkyl, $C_1$-$C_3$-alkoxy, carboxy, carbalkoxy, halogen, trifluoromethyl, hydroxy and mercapto; and pharmaceutically acceptable, non-toxic salts thereof, pharmaceutically-acceptable non-toxic metal complexes thereof or the products wherein the H of —$NHR_4$ is replaced by the acyl group of a carboxylic acid.

2. A compound of the formula I having anti-inflammatory, analgesic or antipyretic activity and characterized by its low acute toxicity and low gastro ulcerogenic activity

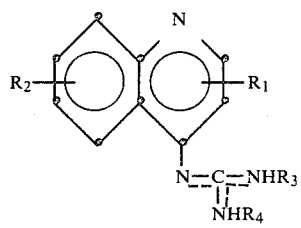

in which $R_1$ represents hydrogen or $C_1$-$C_4$-alkyl; $R_2$ represents hydrogen or $C_1$-$C_4$-alkyl; $R_3$ represents tertiary $C_4$-$C_{12}$-alkyl, $C_5$-$C_7$-cycloalkyl or phenyl, and $R_4$ represents thiazolinyl, thienyl, pyrryl, thiazolyl, isothiazolyl, pyrazolyl, imidazolyl, oxaxolyl, isoxazolyl, triazolyl, thiadiazolyl, tetrazolyl, pyridyl, pyridazinyl, pyrimidyl, pyrazinyl, triazinyl, oxazinyl, benzoxazolyl, benzothiazolyl or benzoimidazolyl; and pharmaceutically acceptable, non-toxic salts thereof, pharmaceutically acceptable, non-toxic metal complexes thereof or the above products wherein the H of $NHR_4$ is replaced by acetyl or propionyl.

3. A compound of the formula I having anti-inflammatory, analgesic or antipyretic activity and characterized by its low acute toxicity and low gastro ulcerogenic activity

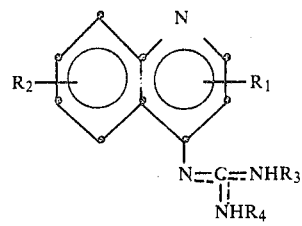

in which $R_1$ represents hydrogen, methyl or ethyl; $R_2$ represents hydrogen; $R_3$ represents tert-butyl, tert-pentyl, cyclohexyl or phenyl; and $R_4$ represents 2-thiazolyl, 2-(4-methyl-thiazolyl), or 2-(5-methyl-1,3,4-thiadiazolyl); and pharmaceutically acceptable, non-toxic salts thereof, pharmaceutically acceptable, non-toxic copper, zinc, manganese, magnesium, iron and gold complexes thereof or the above products wherein the H of the group $NHR_4$ is replaced by acetyl or propionyl.

4. A compound of claim 3 in which $R_1$ is methyl.

5. A compound of formula I of claim 1, in the form of a mono- or di-salt with hydrochloric acid, hydrobromic acid, phosphoric acid, sulfuric acid, nitric acid, carbonic acid, p-toluenesulfonic acid, methanesulfonic acid, formic acid, acetic acid, propionic acid, citric acid, tartaric acid or maleic acid.

6. A compound of formula I of claim 1, or its salt, in the form of a complex formed with a member selected from the group consisting of Cu-, Zn-, Mn-, Mg-, Fe- and Au-salts.

7. N-Cyclohexyl-N''-4-(2-methylquinolyl)-N'-2-thiazolylguanidine and pharmaceutically acceptable, non-toxic salts thereof.

8. N-tert-butyl-N''-4-(2-methylquinolyl)-N'-2-thiazolylguanidine and pharmaceutically acceptable, non-toxic salts thereof.

9. N-tert-butyl-N''-4-(2-methylquinolyl)-N'-2-thiazolinylguanidine and pharmaceutically acceptable, non-toxic salts thereof.

10. N''-4-(2-Methylquinolyl)-N-tert-pentyl-N'-2-thiazolylguanidine and pharmaceutically acceptable, non-toxic salts thereof.

11. N-tert-Butyl-N''-4-(2-methylquinolyl)-N'-2-(4-methylthiazolyl)guanidine and pharmaceutically acceptable, non-toxic salts thereof.

12. N''-4-(2-Methylquinolyl)-N-phenyl-N'-2-thiazolylguanidine and pharmaceutically acceptable, non-toxic salts thereof.

13. N-Acetyl-N'-cyclohexyl-N''-4-(2-methylquinolyl)-N-2-thiazolylguanidine and pharmaceutically acceptable, non-toxic salts thereof.

14. N-Isobutyl-N''-4-(2-methylquinolyl)-N'-2-thiazolylguanidine and pharmaceutically acceptable, non-toxic salts thereof.

15. N-Cycloheptyl-N''-4-(2-methylquinolyl)-N'-2-thiazolylguanidine and pharmaceutically acceptable, non-toxic salts thereof.

16. A pharmaceutical composition in dosage unit form for enteral, parenteral or topical treatment of humans or domestic animals suffering from arthritic diseases, which comprises as an active ingredient 0.01 g to 1 g of a compound as claimed in claim 1 calculated as the free base together with a pharmaceutically acceptable, non-toxic carrier.

17. A pharmaceutical composition in dosage unit form as claimed in claim 16 for oral treatment of humans or domestic animals in which the active ingredient is present in an amount of from 0.025 g to 0.5 g of the active ingredient, calculated as the free base.

18. A pharmaceutical composition in dosage unit form as claimed in claim 17 wherein the active component is the compound N-cyclohexyl-N"-4-(2-methylquinolyl)-N'-2-thiazolylguanidine or a pharmaceutically acceptable, non-toxic salt thereof, non-toxic metal complex thereof, or the products obtained by acylating said thiazolylguanidine with a carboxylic acid.

19. A pharmaceutical preparation in dosage unit form as claimed in claim 18 in the form of tablets, pills or capsules.

20. A pharmaceutical composition in dosage unit form for parenteral treatment of humans or domestic animals suffering from arthritic diseases comprising, as an active ingredient, from 0.1 g to 1 g of a compound as claimed in claim 1, calculated as the free base, as such or in the form of one of its non-toxic salts, non-toxic metal complexes or the products obtained by acylating said compound with a carboxylic acid, together with a pharmaceutically acceptable carrier.

21. A pharmaceutical composition comprising, as an active ingredient, a compound as claimed in claim 1 together with a carrier, the active ingredient being present in an amount from 0.1% to 95%, calculated as the free base, of said composition.

22. A pharmaceutical composition as claimed in claim 19 wherein the active ingredient is present together with a further antiinflammatory, analgetic or antipyretic agent, and a pharmaceutically acceptable, non-toxic carrier.

23. A pharmaceutical composition in dosage unit form as claimed in claim 20 for enteral and parenteral treatment of humans or domestic animals comprising from 0.01 g to 1 g in total of said active ingredient present in the composition.

24. A composition for topical treatment in the form of a powder or an ointment or cream comprising at least one compound as defined in claim 1 in an amount of from 0.5 g to 10 g per 100 g of the preparation, together with an inert pharmaceutically acceptable carrier.

25. In the treatment of humans or domestic animals suffering from arthritic diseases, the administration of a compound as claimed in claim 1, alone or in combination with another active ingredient, in daily doses from 1 mg/kg body weight/day to 30 mg/kg body weight/day of the active ingredient(s).

* * * * *